US012295600B2

(12) United States Patent
Stigall et al.

(10) Patent No.: US 12,295,600 B2
(45) Date of Patent: May 13, 2025

(54) INTRALUMINAL ULTRASOUND DEVICE FOR DIAGNOSTIC IMAGING AND THERAPY

(71) Applicant: KONINKLIJKE PHILIPS N.V., Eindhoven (NL)

(72) Inventors: Jeremy Stigall, Carlsbad, CA (US); Princeton Saroha, Ladera Ranch, CA (US); Robert Emmett Kearney, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 580 days.

(21) Appl. No.: 16/103,578

(22) Filed: Aug. 14, 2018

(65) Prior Publication Data

US 2019/0054323 A1 Feb. 21, 2019

Related U.S. Application Data

(60) Provisional application No. 62/545,944, filed on Aug. 15, 2017.

(51) Int. Cl.
*A61B 17/22* (2006.01)
*A61B 8/00* (2006.01)
(Continued)

(52) U.S. Cl.
CPC .......... *A61B 17/22012* (2013.01); *A61B 8/12* (2013.01); *A61B 8/445* (2013.01);
(Continued)

(58) Field of Classification Search
CPC ........ A61B 17/22012; A61B 17/22004; A61B 8/56; A61B 8/12; A61B 8/445;
(Continued)

(56) References Cited

U.S. PATENT DOCUMENTS 5,304,115 A 4/1994 Pflueger et al.
5,486,170 A 1/1996 Winston et al.
(Continued)

FOREIGN PATENT DOCUMENTS

WO 1995019143 A1 7/1995
WO 20080623434 A1 5/2008
WO WO-2016170446 A1 * 10/2016 ........... A61B 5/0066

OTHER PUBLICATIONS

Phased Array Imaging and Therapy Intraluminal Ultrasound Drive, U.S. Appl. No. 62/545,951, filed Aug. 15, 2017.
(Continued)

*Primary Examiner* — Joseph M Santos Rodriguez
*Assistant Examiner* — Zainab Mohammed Aldarraji

(57) ABSTRACT

An intraluminal ultrasound device includes a flexible elongate member configured to be inserted into a lumen of a patient, the flexible elongate member comprising a proximal portion and a distal portion, an ultrasound imaging assembly disposed at the distal portion of the flexible elongate member, the ultrasound imaging assembly configured to obtain imaging data while positioned within the lumen of the patient; and a radiating member disposed at the distal portion of the flexible elongate member and in communication with an ultrasound transducer positioned outside of the patient, wherein the radiating member configured to transmit ultrasound energy from the ultrasound transducer within the lumen of the patient to apply an ultrasound therapy. Associated devices, systems and methods are also provided.

21 Claims, 6 Drawing Sheets

(51) Int. Cl.
*A61B 8/12* (2006.01)
*A61B 8/08* (2006.01)
*A61B 90/00* (2016.01)
*A61M 37/00* (2006.01)
*A61N 7/00* (2006.01)

(52) U.S. Cl.
CPC .............. *A61B 8/4494* (2013.01); *A61B 8/56* (2013.01); *A61B 17/22004* (2013.01); *A61B 8/0891* (2013.01); *A61B 8/4483* (2013.01); *A61B 2017/22008* (2013.01); *A61B 2017/22018* (2013.01); *A61B 2017/22084* (2013.01); *A61B 2090/3784* (2016.02); *A61M 37/0092* (2013.01); *A61N 7/00* (2013.01); *A61N 2007/0043* (2013.01); *A61N 2007/0052* (2013.01)

(58) Field of Classification Search
CPC ........ A61B 8/4494; A61B 2017/22018; A61B 2017/22008; A61B 2017/22084; A61B 8/4483; A61B 8/0891; A61B 2090/3784; A61B 17/2202; A61B 17/3207; A61B 17/320758; A61M 37/0092; A61N 7/00; A61N 2007/0043; A61N 2007/0052; A61N 2007/0095; A61N 7/022
See application file for complete search history.

(56) References Cited

U.S. PATENT DOCUMENTS

| | | | | |
|---|---|---|---|---|
| 5,630,837 | A * | 5/1997 | Crowley | A61B 8/12 601/2 |
| 6,066,096 | A * | 5/2000 | Smith | A61B 8/4488 600/439 |
| 6,200,268 | B1 | 3/2001 | Vince | |
| 6,381,350 | B1 | 4/2002 | Klingensmith | |
| 6,537,306 | B1 * | 3/2003 | Burdette | A61B 18/18 600/459 |
| 7,074,188 | B2 | 7/2006 | Nair | |
| 7,175,597 | B2 | 2/2007 | Vince | |
| 7,215,802 | B2 | 5/2007 | Klingensmith | |
| 7,359,554 | B2 | 4/2008 | Klingensmith | |
| 7,463,759 | B2 | 12/2008 | Klingensmith | |
| 8,936,553 | B2 * | 1/2015 | Stigall | A61B 17/22 600/439 |
| 10,226,203 | B2 * | 3/2019 | Stigall | A61B 1/05 |
| 10,238,367 | B2 * | 3/2019 | Stigall | A61B 8/0891 |
| 10,687,832 | B2 * | 6/2020 | Stigall | A61B 17/2202 |
| 2001/0020126 | A1 * | 9/2001 | Swanson | A61B 8/445 600/407 |
| 2004/0024393 | A1 * | 2/2004 | Nita | A61B 17/2202 606/28 |
| 2004/0049148 | A1 * | 3/2004 | Rodriguez | A61N 7/00 600/467 |
| 2007/0073135 | A1 * | 3/2007 | Lee | A61B 8/483 600/407 |
| 2007/0233040 | A1 * | 10/2007 | Macnamara | A61B 1/0055 604/523 |
| 2008/0007142 | A1 * | 1/2008 | Toda | G10K 11/28 310/335 |
| 2008/0086073 | A1 * | 4/2008 | McDaniel | A61B 18/1492 604/22 |
| 2011/0257523 | A1 | 10/2011 | Hastings | |
| 2013/0267848 | A1 * | 10/2013 | Fearnot | A61B 8/0841 606/200 |
| 2014/0058251 | A1 * | 2/2014 | Stigall | A61B 6/12 600/407 |
| 2014/0088630 | A1 * | 3/2014 | Tran | A61N 7/022 606/169 |
| 2014/0378873 | A1 * | 12/2014 | Chernomorsky | A61M 37/0092 601/2 |
| 2015/0342625 | A1 * | 12/2015 | Shimizu | A61B 17/2202 606/128 |
| 2016/0113633 | A1 * | 4/2016 | Hadjicostis | A61B 8/56 600/439 |
| 2016/0262777 | A1 * | 9/2016 | Stigall | A61B 17/3203 |
| 2016/0287278 | A1 * | 10/2016 | Stigall | A61B 17/2202 |
| 2016/0302762 | A1 * | 10/2016 | Stigall | A61B 8/12 |
| 2017/0325696 | A1 * | 11/2017 | Yoshida | A61B 5/4848 |
| 2019/0053785 | A1 * | 2/2019 | Stigall | A61B 8/12 |
| 2020/0000525 | A1 * | 1/2020 | Stigall | A61B 8/445 |
| 2020/0289085 | A1 * | 9/2020 | Stigall | A61B 8/4236 |

OTHER PUBLICATIONS

Intracardiac Therapeutic and Diagnostic Ultrasound Device, U.S. Appl. No. 62/545,927, filed Aug. 15, 2017.
Frequency-Tunable Intraluminal Ultrasound Device, U.S. Appl. No. 62/545,954, filed Aug. 15, 2017.
Intraluminal Rotational Ultrasound for Diagnostic Imaging and Therapy, U.S. Appl. No. 62/545,888, filed Aug. 15, 2017.

* cited by examiner

INTRALUMINAL ULTRASOUND DEVICE FOR DIAGNOSTIC IMAGING AND THERAPY

TECHNICAL FIELD

The present disclosure relates generally to preparing an anatomy of a patient for a pharmacological treatment. Specifically, the disclosure relates to preparing the patient for a pharmacological treatment using an ultrasound device capable of emitting a dual band ultrasonic frequency range within the anatomy of a patient to create an image of and provide therapy to the anatomy.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy with frequencies higher than 10 MHz to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Ultrasound has been used in some drug delivery and therapeutic applications. Conventionally, due to the different in operation frequencies between the two, an ultrasound imaging device and an ultrasound therapeutic device are separate and distinct. In the case of intravascular imaging and therapy, both the ultrasound imaging device and the ultrasound therapeutic device have to be inserted into and withdrawn from the patient's blood vessel at least once during a procedure workflow. To evaluate the effectiveness of an ultrasound therapy, the intravascular therapy device has to be withdrawn from the patient's blood vessel, and the imaging device has to be re-inserted in to the blood vessel. This multiplicity of insertion and withdrawal of ultrasound devices not only is time-consuming but also can increase chances of clinical complications, such as blood vessel damage.

SUMMARY

Embodiments of the present disclosure provide an ultrasound device with combined ultrasound imaging and ultrasound therapy components. For example, the ultrasound device may include imaging assembly with an internal ultrasound transducer that is sized and shaped to be positioned within blood vessels of a patient or any other suitable parts of the patient body. Further, the ultrasound device may include at therapeutic intermediate member, positioned adjacent the imaging assembly, which functions to emit low frequency therapeutic ultrasound energy into the patient. The low frequency therapeutic ultrasound energy is generated from an external transducer positioned outside of the patient, which conveys the therapeutic ultrasound energy to the therapeutic intermediate member within the patient. The systems, devices and methods described herein advantageously allow for ultrasound imaging and ultrasound therapy components to be provided on the same device such that the multiple devices do not need to be inserted and removed for imaging and therapy. This advantageously improves the medical workflow for the patient and the physician.

According to aspects of the present disclosure an intraluminal ultrasound device is provided. The intraluminal ultrasound device includes a flexible elongate member configured to be inserted into a lumen of a patient, the flexible elongate member comprising a proximal portion and a distal portion; an ultrasound imaging assembly disposed at the distal portion of the flexible elongate member, the ultrasound imaging assembly configured to obtain imaging data while positioned within the lumen of the patient; and a radiating member disposed at the distal portion of the flexible elongate member and in communication with an ultrasound transducer positioned outside of the patient, wherein the radiating member configured to transmit ultrasound energy from the ultrasound transducer within the lumen of the patient to apply an ultrasound therapy.

In some aspects, the ultrasound imaging assembly comprises at least one of circumferential transducer array, a planar transducer array, or a rotating transducer. In some aspects, the ultrasound imaging assembly is configured to emit ultrasound energy at a frequency range between 10 MHz and 70 MHz. In some aspects, the radiating member is mechanically and acoustically coupled to the ultrasound transducer. In some aspects, the radiating member is configured to emit ultrasound energy at a frequency range between 1 KHz and 5 MHz. In some aspects, the radiating member comprises a circumferential band configured to emit the ultrasound energy. In some aspects, the radiating member further comprises a connecting member extending longitudinally between consecutive circumferential bands of the plurality of circumferential bands. In some aspects, the radiating member further comprises a plurality of connecting members extending longitudinally between the consecutive circumferential bands of the plurality of circumferential bands. In some aspects, the connecting member comprises a plurality of notches. In some aspects, the plurality of notches is disposed on opposing first and second sides of the connecting member.

According to aspects of the present disclosure, an ultrasound method is provided. The method includes obtaining ultrasound imaging data using an ultrasound imaging assembly and disposed at a distal portion of a flexible elongate member positioned within a lumen of a patient applying an ultrasound therapy to the lumen of the patient using a radiating member in communication with an ultrasound transducer positioned outside of the patient, the radiating member disposed at the distal portion of the flexible elongate member and configured to transmit ultrasound energy from the ultrasound transducer within the lumen of the patient.

In some aspects, the method further comprises generating, at a computer in communication with the ultrasound imaging assembly, at an intravascular ultrasound (IVUS) image of the lumen based on the ultrasound imaging data; and outputting the IVUS image to a display in communication with the computer. In some aspects, the method further comprises evaluating, at the computer, obtained ultrasound imaging data of the lumen; and determining, at the computer, a parameter for the ultrasound therapy based on the evaluating. In some aspects, the method further comprises applying the ultrasound therapy includes applying the ultrasound therapy based on the determined parameter. In some aspects, the method further comprises determining a parameter of at least one of a frequency, pulse amplitude, or a pulse length of the ultrasound energy. In some aspects, the method further comprises controlling, by the computer, the external ultrasound transducer to emit ultrasound energy based on the determined parameter. In some aspects, the method further comprises transmitting the emitted ultrasound energy from the external ultrasound transducer to the radiating member via an acoustic coupling member. In some aspects, the method further comprises applying a pharmacological agent to the lumen.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
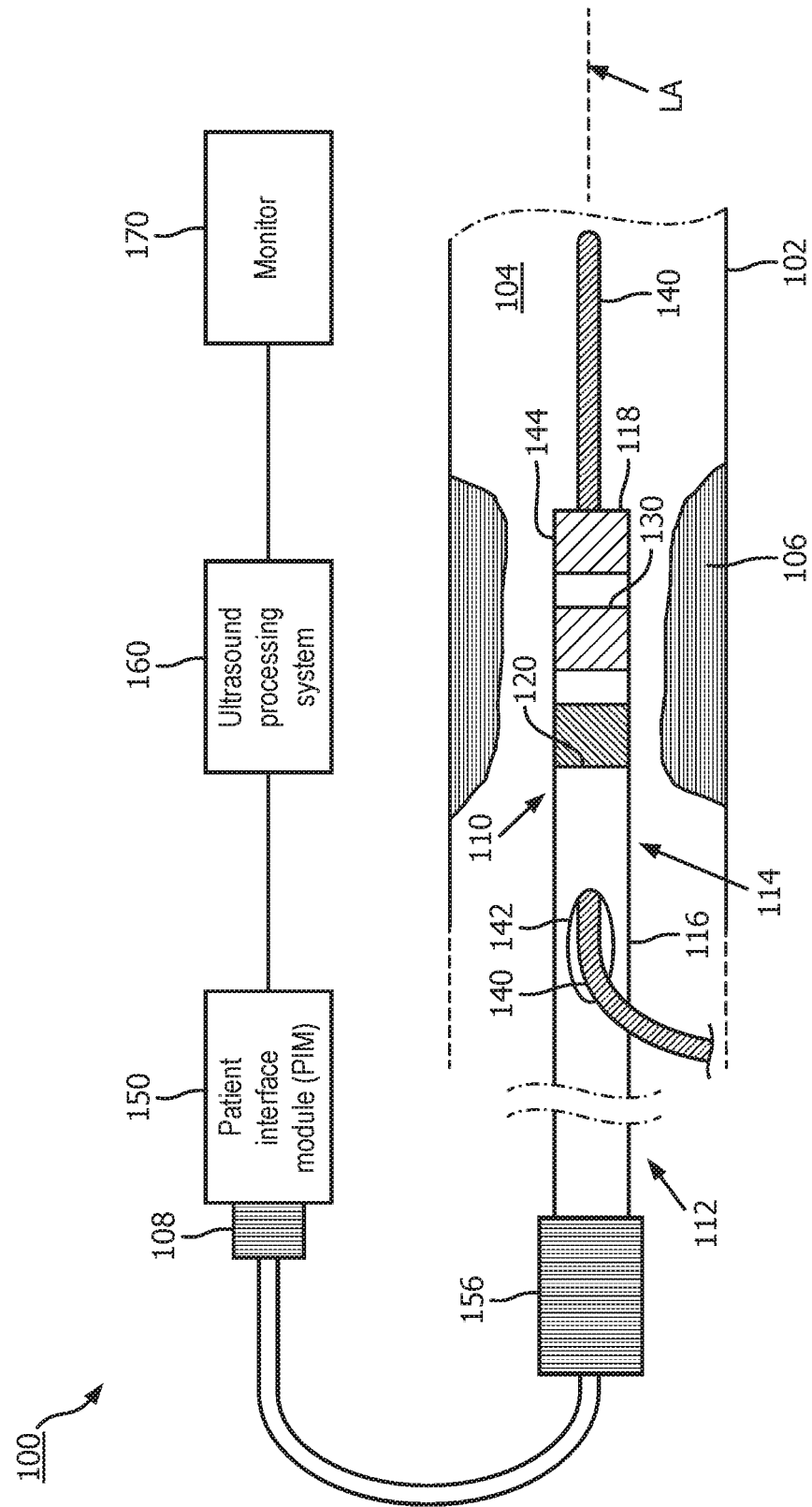
FIG. 1 is a diagrammatic schematic view of an ultrasound system according to some embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an ultrasound system 100 according to some embodiments of the present disclosure. The ultrasound system 100 can include an ultrasound device 110, a patient interface module (PIM) 150, an ultrasound processing system 160, and/or a monitor 170. As discussed further herein, in certain embodiments, elements of the ultrasound device 110 are structurally arranged (e.g., sized and/or shaped) to be positioned within anatomy 102 of a patient. The ultrasound device 110 obtains ultrasound imaging data from within the anatomy 102 and applies ultrasound therapy to the anatomy 102. The ultrasound processing system 160, which in some embodiments is a computer, can control the acquisition of ultrasound imaging data and/or the application of ultrasound therapy, and generates an image of the anatomy 102 (using the ultrasound imaging data received via the PIM 150) that is displayed on the monitor 170.

Generally, the ultrasound device 110 can be a catheter, a guide catheter, or a guide wire. The ultrasound device 110 includes a flexible elongate member 116. As used herein, "elongate member" or "flexible elongate member" includes at least any thin, long, flexible structure structurally arranged (e.g., sized and/or shaped) to be positioned within a lumen 104 of the anatomy 102. For example, a distal portion 114 of the flexible elongate member 116 is positioned within the lumen 104, while a proximal portion 112 of the flexible elongate member 116 is positioned outside of the body of the patient. The flexible elongate member 116 can include a longitudinal axis LA. In some instances, the longitudinal axis LA can be a central longitudinal axis of the flexible elongate member 116. In some embodiments, the flexible elongate member 116 can include one or more polymer/plastic layers formed of various grades of nylon, Pebax, polymer composites, polyimides, and/or Teflon. In some embodiments, the flexible elongate member 116 can include one or more layers of braided metallic and/or polymer strands. The braided layer(s) can be tightly or loosely braided in any suitable configuration, including any suitable per in count (pic). In some embodiments, the flexible elongate member 116 can include one or more metallic and/or polymer coils. All or a portion of the flexible elongate member 116 may have any suitable geometric cross-sectional profile (e.g., circular, oval, rectangular, square, elliptical, etc.) or non-geometric cross-sectional profile. For example, the flexible elongate member 116 can have a generally cylindrical profile with a circular cross-sectional profile that defines an outer diameter of the flexible elongate member 116. For example, the outer diameter of the flexible elongate member 116 can be any suitable value for positioning within the anatomy 102, including between approximately 1 Fr (0.33 mm) and approximately 15 Fr (5 mm), including values such as 3.5 Fr, 5 Fr, 7 Fr, 8.2 Fr, 9 Fr, and/or other suitable values both larger and smaller.

The ultrasound device 110 may or may not include one or more lumens extending along all or a portion of the length of the flexible elongate member 116. The lumen of the ultrasound device 110 can be structurally arranged (e.g., sized and/or shaped) to receive and/or guide one or more other diagnostic and/or therapeutic instruments. If the ultrasound device 110 includes lumen(s), the lumen(s) may be centered or offset with respect to the cross-sectional profile of the ultrasound device 110. In the illustrated embodiment, the ultrasound device 110 is a catheter and includes a lumen at the distal portion 114 of the flexible elongate member 116. A guide wire 140 extends through the lumen of the ultrasound device 110 between an entry/exit port 142 and an exit/entry port at a distal end 118 of the flexible elongate member 116. Generally, the guide wire 140 is a thin, long, flexible structure that is structurally arranged (e.g., sized and/or shaped) to be disposed within the lumen 104 of the anatomy 102. During a diagnostic and/or therapeutic procedure, a medical professional typically first inserts the guide wire 140 into the lumen 104 of the anatomy 102 and moves the guide wire 140 to a desired location within the anatomy 102, such as adjacent to an occlusion 106. The guide wire 140 facilitates introduction and positioning of one or more other diagnostic and/or therapeutic instruments, including the ultrasound device 110, at the desired location within the anatomy 102. For example, the ultrasound device 110 moves through the lumen 104 of the anatomy 102 along the guide wire 140. In some embodiments, the lumen of the ultrasound device 110 can extend along the entire length of the flexible elongate member 116. In the illustrated embodiment, the entry/exit port 142 is positioned proximally of ultrasound structures 120, 130, and 144 of the ultrasound device 110. In some embodiments, the exit/entry port 142, the exit/entry port at the distal end 118, and/or the lumen of the ultrasound device 110 is positioned distally of the ultrasound structures 120, 130, and 144. In some embodiments, the ultrasound device 110 is not used with a guide wire, and the exit/entry port 142 can be omitted from the ultrasound device 110.

The anatomy 102 may represent any fluid-filled or surrounded structures, both natural and man-made. For example, the anatomy 102 can be within the body of a patient. Fluid can flow through the lumen 104 of the anatomy 102. In some instances, the ultrasound device 110 can be referenced as an intraluminal device. The anatomy 102 can be a vessel, such as a blood vessel, in which blood flows through the lumen 104. In some instances, the ultrasound device 110 can be referenced as an intravascular device. In various embodiments, the blood vessel is an artery or a vein of a patient's vascular system, including cardiac vasculature, peripheral vasculature, neural vasculature, renal vasculature, and/or any other suitable anatomy/lumen inside the body. The anatomy 102 can be tortuous in some instances. For example, the ultrasound device 110 may be used to examine any number of anatomical locations and tissue types, including without limitation, organs including the liver, heart, kidneys, gall bladder, pancreas, lungs, esophagus; ducts; intestines; nervous system structures including the brain, dural sac, spinal cord and peripheral nerves; the urinary tract; as well as valves within the blood, chambers or other parts of the heart, and/or other systems of the body. In addition to natural structures, the ultrasound device 110 may be used to examine man-made structures such as, but without limitation, heart valves, stents, shunts, filters and other devices.

The occlusion 106 of the anatomy 102 is generally representative of any blockage or other structural arrangement that results in a restriction to the flow of fluid through the lumen 104, for example, in a manner that is deleterious to the health of the patient. For example, the occlusion 106 narrows the lumen 104 such that the cross-sectional area of the lumen 104 and/or the available space for fluid to flow through the lumen 104 is decreased. Where the anatomy 102 is a blood vessel, the occlusion 106 may be a result of plaque buildup, including without limitation plaque components such as fibrous, fibro-lipidic (fibro fatty), necrotic core, calcified (dense calcium), blood, fresh thrombus, and/or mature thrombus. In some instances, the occlusion 106 can be referenced as thrombus, a stenosis, and/or a lesion. Generally, the composition of the occlusion 106 will depend on the type of anatomy being evaluated. Healthier portions of the anatomy 102 may have a uniform or symmetrical profile (e.g., a cylindrical profile with a circular cross-sectional profile). The occlusion 106 may not have a uniform or symmetrical profile. Accordingly, diseased portions of the anatomy 102, with the occlusion 106, will have a non-symmetric and/or otherwise irregular profile. While the anatomy 102 is illustrated in FIG. 1 as having a single occlusion 106, it is understood that the devices, systems, and methods described herein have similar application for anatomy having multiple occlusions.

The ultrasound device 110 includes ultrasound structures 120 and 130 at the distal portion 114 of the flexible elongate member 116. The ultrasound structures 120 and 130 are configured to emit ultrasonic energy into the anatomy 102 while the ultrasound system 100 is positioned within the lumen 104. In some embodiments, the two ultrasound structures 120 and 130 are distinct. In other embodiments, the two ultrasound structures 120 and 130 are the same ultrasound component or part of the same ultrasound component. One of the ultrasound structures 120, 130 is configured for diagnostic use, while the other of the ultrasound structures 120, 130 is configured for therapeutic use. For example, the ultrasound structures 120, 130 can emit different frequencies of ultrasonic energy into the anatomy 102 depending on whether the ultrasonic energy is being used for diagnosis, such as imaging, and/or treatment.

In some embodiments, the ultrasound structures 120 and/or 130 include ultrasound transducer(s). For example, the ultrasound structures 120 and/or 130 can be configured to generate and emit ultrasound energy into the anatomy 102 in response to being activated by an electrical signal. In some embodiments, the ultrasound structures 120 and/or 130 include a single ultrasound transducer. In some embodiments, the ultrasound structures 120 and/or 130 include an ultrasound transducer array including more than one ultrasound transducer. For example, an ultrasound transducer array can include any suitable number of individual transducers between 2 transducers and 1000 transducers, including values such as 2 transducers, 4 transducers, 36 transducers, 64 transducers, 128 transducers, 500 transducers, 812 transducers, and/or other values both larger and smaller. The ultrasound structures 120 and/or 130 can be any suitable configuration, such as phased array including a planar array, a curved array, a circumferential array, an annular array, etc. For example, the ultrasound structures 120 and/or 130 can be a one-dimensional array or a two-dimensional array in some instances. In some instances, the ultrasound structures 120 and/or 130 can be a rotational ultrasound device. The active area of the ultrasound structures 120 and/or 130 can include one or more transducer materials and/or one or more segments of ultrasound elements (e.g., one or more rows, one or more columns, and/or one or more orientations) that can be uniformly or independently controlled and activated. The active area of the ultrasound structures 120 and/or 130 can be patterned or structured in various basic or complex geometries. The ultrasound structures 120 and/or 130 can be disposed in a side-looking orientation (e.g., ultrasonic energy emitted perpendicular and/or orthogonal to the longitudinal axis LA) and/or a forward-looking looking orientation (e.g., ultrasonic energy emitted parallel to and/or along the longitudinal axis LA). In some instances, the ultrasound structures 120 and/or 130 is structurally arranged to emit and/or receive ultrasonic energy at an oblique angle relative to the longitudinal axis LA, in a proximal or distal direction. In some embodiments, ultrasonic energy emission can be electronically steered by selective triggering of one or more transducer elements of the ultrasound structure 120 and/or 130.

The ultrasound transducer(s) of the ultrasound structures 120 and/or 130 can be a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. Depending on the transducer material, the manufacturing process for ultrasound transducer(s) can include dicing, kerfing, grinding, sputtering, wafer technologies (e.g., SMA, sacrificial layer deposition), other suitable processes, and/or combinations thereof.

In some embodiments, the ultrasound structure 120 is configured to obtain ultrasound imaging data associated with the anatomy 102, such as the occlusion 106. The ultrasound imaging data obtained by the ultrasound structure 120 can be used by a medical professional to diagnose the patient, including evaluating the occlusion 106 of the anatomy 102. For imaging, the ultrasound structure 120 can be configured to both emit ultrasonic energy into the lumen 104 and/or the anatomy 102, and to receive reflected ultrasound echoes representative of fluid and/or tissue of lumen 104 and/or the anatomy 102. As described herein, the ultrasound structure 120 can be an ultrasound imaging element, such as an ultrasound transducer and/or an ultrasound transducer array. For example, the ultrasound structure 120 generates and emits ultrasound energy into the anatomy 102 in response to transmission of an electrical signal to the ultrasound structure 120. For imaging, the ultrasound imaging structure 120 generates and transmits an electrical signal representative of the received reflected ultrasound echoes from the anatomy 102 (e.g., to the PIM 150 and/or computer 160). In various embodiments, the ultrasound structure 120 can obtain imaging data associated with intravascular ultrasound (IVUS) imaging, forward looking intravascular ultrasound (FL-IVUS) imaging, intravascular photoacoustic (IVPA) imaging, intracardiac echocardiography (ICE), transesophageal echocardiography (TEE), and/or other suitable imaging modalities.

For diagnosis and/or imaging, the center frequency of the ultrasound structure 120 can be between 10 MHz and 70 MHz, for example, including values such as 10 MHz, 20 MHz, 40 MHz, 45 MHz, 60 MHz, and/or other suitable values both larger and smaller. For example, lower frequencies (e.g., 10 MHz, 20 MHz) can advantageously penetrate further into the anatomy 102, such that more of the anatomy 102 is visible in the ultrasound images. Higher frequencies (e.g., 45 MHz, 60 MHz) can be better suited to generate more detailed ultrasound images of the anatomy 102 and/or fluid within the lumen 104. In some embodiments, the frequency of the ultrasound structure 120 is tuneable. For imaging, in some instances, the ultrasound structure 120 can be tuned to receive wavelengths associated with the center frequency and/or one or more harmonics of the center frequency. In some instances, the frequency of the emitted ultrasonic energy can be modified by the voltage of the applied electrical signal and/or the application of a biasing voltage to the ultrasound structure 120.

In some embodiments, the structure 130 is configured to apply an ultrasound therapy to the anatomy 102, such as the occlusion 106. For example, the structure 130 emits sound waves that damage the structure of the occlusion 106. In that regard, the ultrasound device 110 and/or the structure 130 can be referenced as a lithotripsy device. The ultrasonic energy emitted by the structure 130 can create micro fractures in the occlusion 106. For example, the structure 130 can deliver ultrasonic energy in a targeted manner to cause cavitation (e.g., wave force cavitation, thermal cavitation, etc.) of the occlusion 106. Delivery of ultrasound therapy by the structure 130 advantageously facilitates thrombus dilution and/or vessel preparation. For example, ultrasound therapy can be applied prior to delivery of a pharmacological agent to the anatomy 102. The pharmacological agent can be a thrombolytic agent, a fibrinolytic agent, plasmin, plasmid, tissue plasminogen activator, urokinase, streptokinase, collagenace, hepranoid, anti-thrombin drug, any other suitable drug, and/or combinations thereof. As described herein, Pharmacological uptake can be advantageously improved as a result of the degradation of the occlusion 106 by the ultrasonic energy. By compromising the structure of the occlusion 106, additional surface area is available for the pharmacological agent to contact and/or penetrate the anatomy 102. Accordingly, the efficacy of the treatment and the health of the patient is improved.

In some embodiments, the structure 130 is an ultrasound element, such as an ultrasound transducer and/or ultrasound transducer array. For example, the ultrasound imaging element 130 can be configured to generate and emit ultrasound energy into the anatomy 102 in response to transmission of an electrical signal to the structure 130. Unlike the ultrasound structure 120, which is used of ultrasound imaging, the structure 130 need not be configured to receive ultrasonic echoes reflected the anatomy 102 and generate a representative electrical signal. For example, in some embodiments, the structure 130 is not an ultrasound element that generates ultrasound energy. Rather, the structure 130 can be an intermediate component that is configured to deliver ultrasound energy generated by an ultrasound component separate from the ultrasound device 110 (e.g., an external ultrasound transducer positioned outside of the body of the patient). For ultrasound therapy, the center frequency of the ultrasound structure 130 can be between 1 kHz and 5 MHz, for example, including values such as 50 kHz, 500 kHz, 1 MHz, 3 MHz, and/or other suitable values both larger and smaller. In some embodiments, the frequency of the ultrasound structure 130 is tuneable. For example, the frequency of the emitted ultrasonic energy can be modified by the voltage of the applied electrical signal and/or the application of a biasing voltage to the ultrasound structure 130.

In some embodiments, such as when the ultrasound structures 120 and 130 both include ultrasound transducers, the ultrasound structures 120 and 130 can be configured to generate and to emit ultrasound energy, and to generate electrical signals representative of the received ultrasound echoes. One of the ultrasound structures 120, 130 can be operated in diagnostic and/or imaging mode (generates and emits ultrasound energy, and generates electrical signals representative of the received ultrasound echoes), while the other of the ultrasound structures 120, 130 is operated in therapeutic mode (generates and/or emits ultrasound energy).

In some embodiments, the ultrasound device 110 includes a treatment component 144. For example, the treatment component 144 can include a balloon, a stent, a needle, an ablation electrode, mechanical cutting component, a rotational cutting device, an aspiration device, and/or other suitable devices. The treatment component 144 can be a targeted drug delivery device, a drug coated balloon, a drug coated stent, and/or other suitable device configured to deliver a pharmacological agent to the anatomy 102, such as the occlusion 106. For example, the pharmacological agent can be delivered to the anatomy 102 by the treatment component 144 after the ultrasound therapy is applied to the anatomy 102 by the ultrasound structure 130 and/or simultaneously. In other embodiments, the ultrasound device 110 omits the treatment component 144.

Generally, the ultrasound structures 120, 130, and/or 144 are positioned at the distal portion of the flexible elongate member 116. The relative positioning of the ultrasound structures 120, 130, and/or 140 can vary in different embodiments. In the illustrated embodiment, the diagnostic and/or imaging ultrasound structure 120 is positioned proximally of the therapeutic ultrasound structure 130. In other embodiments, the therapeutic ultrasound structure 130 is positioned proximally of the diagnostic and/or imaging ultrasound structure 120. In embodiments which include the treatment component 144, the treatment component 144 can be positioned proximally of the ultrasound structures 120 and/or 130, distally of the ultrasound structures 120 and/or 130, or between the ultrasound structures 120 and/or 130.

The ultrasound structures 120 and/or 130 can include one or more electrical conductors extending along the length from the flexible elongate member 116. The electrical conductor(s) are in communication with the ultrasound structures 120, 130 at the distal portion 114, and an interface 156 at the proximal portion 112. The electrical conductors carry electrical signals between the ultrasound processing system 160 and the ultrasound structures 120, 130. For example, activation and/or control signals can be transmitted from the computer 160 to the ultrasound structures 120, 130 via the electrical conductors. Electrical signals representative of the reflected ultrasound echoes can be transmitted from the ultrasound structures 120 and/or 130 to the computer 160 via the electrical conductors. In some embodiments, the same electrical conductors can be used for communication between the computer 160 and the ultrasound structures 120 and/or 130. In other embodiments, different electrical conductors of the ultrasound device 110 can be used for communication between the computer 160 and the ultrasound structure 120, and between the computer 160 and the ultrasound structure 130.

The ultrasound device 110 includes an interface 156 at the proximal portion 112 of the flexible elongate member 116. In some embodiments, the interface 156 can include a handle. For example, handle can include one or more actuation mechanisms to control movement of the ultrasound device 110, such as deflection of the distal portion 114. In some embodiments, the interface 156 can include a telescoping mechanism that allows for pullback of the ultrasound device 110 through the lumen 104. In some embodiments, the interface 156 can include a rotation mechanism to rotate one or more components of the ultrasound device 110 (e.g., the flexible elongate member 116, the ultrasound structures 120, 130). In some embodiments, the interface 156 includes a user interface component (e.g., one or more buttons, a switch, etc.) for a medical professional to selectively activate the ultrasound structure 120 for imaging or the ultrasound structure 130 for therapy. In other embodiments, a user interface component of the PIM 150, the computer 160 and/or the monitor 170 allows a medical profession to selectively activate the ultrasound structure 120 for imaging or the ultrasound structure 130 for therapy. A conduit including, e.g., electrical conductors, extends between the interface 156 and the connector 108. The connector 108 can be configured to mechanically and/or electrically couple the ultrasound device 110 to the PIM 150.

The ultrasound processing system 160, the PIM 150, and/or the intravascular ultrasound device 110 (e.g., the interface 156, the ultrasound structures 120 and/or 130, etc.) can include one or more controllers. The controllers can be integrated circuits, such as application specific integrated circuits (ASIC), in some embodiments. The controllers can be configured to select the particular transducer element(s) to be used for transmit and/or receive, to provide the transmit trigger signals to activate the transmitter circuitry to generate an electrical pulse to excite the selected transducer element(s), and/or to accept amplified echo signals received from the selected transducer element(s) via amplifiers of controllers. Multiple ASIC configurations with various numbers of master circuits and slave circuits can be used to create a single ultrasound wave or multi-firing ultrasound wave device.

In some embodiments, the PIM 150 performs preliminary processing of the ultrasound echo data prior to relaying the data to the computer or console. In examples of such embodiments, the PIM 150 performs amplification, filtering, and/or aggregating of the data. In an embodiment, the PIM 150 also supplies high- and low-voltage DC power to support operation of the ultrasound device 110 including circuitry associated with the ultrasound structures 120 and/ or 130.

The PIM 150 can be an isolation device as, in various surgical settings; patient safety requirements mandate physical and electrical isolation of the patient from one or more high voltage components.

The ultrasound processing system 160 receives imaging data (e.g., electrical signals representative of the ultrasound echo data) from the ultrasound structure 120 by way of the PIM 150. The computer 160 can include processing circuit, such as processor and/or memory. The ultrasound processing system 160 processes the data to reconstruct an image of the anatomy. The computer 160 outputs image data such that an image of the anatomy 102, such as a cross-sectional IVUS image of a vessel, is displayed on the monitor 170. The computer 160 and/or the monitor 170 can include one or more user interface elements (e.g., touchscreen, keyboard, mouse, virtual buttons on a graphical user interface, physical buttons, etc.) to allow a medical professional to control the ultrasound device 110, including one or more parameters of the ultrasound structures 120, 130.

Figure 2A:
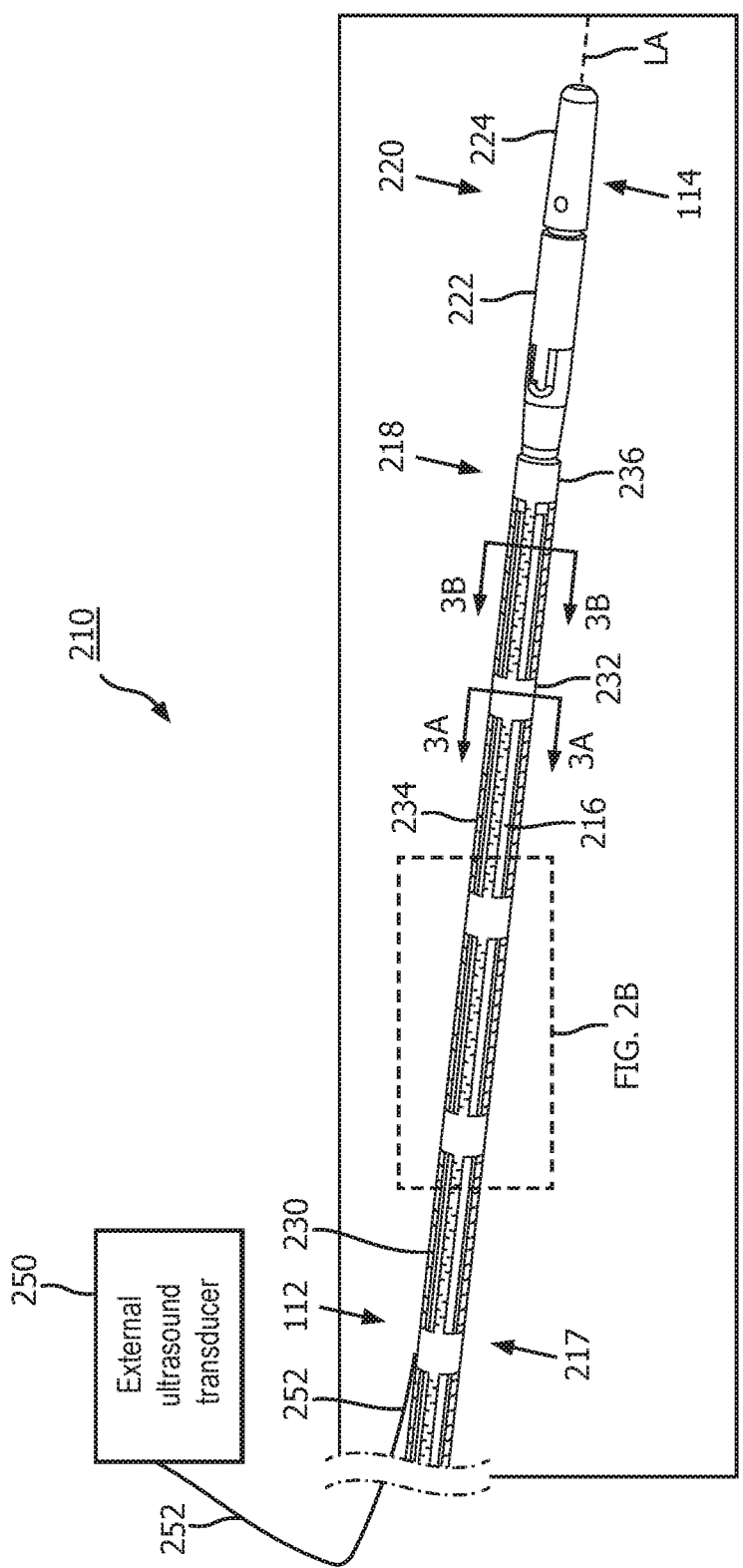
FIG. 2A is diagrammatic schematic view of an intraluminal ultrasound device of the ultrasound system according to embodiments of the present disclosure.

FIG. 2A is a diagrammatic, schematic view of an embodiment of an intraluminal ultrasound device 210 of the ultrasound system 100. Similar to the ultrasound device 110 described with respect to FIG. 1, the intraluminal ultrasound device 210 is positioned along the distal portion 114 of the ultrasound system 100 within the lumen 104 of the anatomy 102.

Figure 4A:
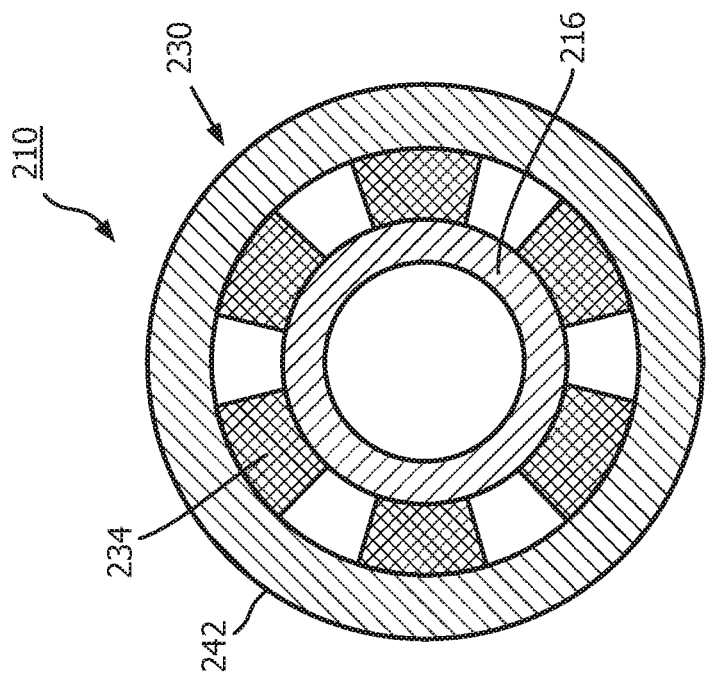
FIG. 4A is a cross sectional view of the therapeutic intermediate member similar to FIG. 3A and including an outer sleeve according to embodiments of the present disclosure.
Figure 4B:
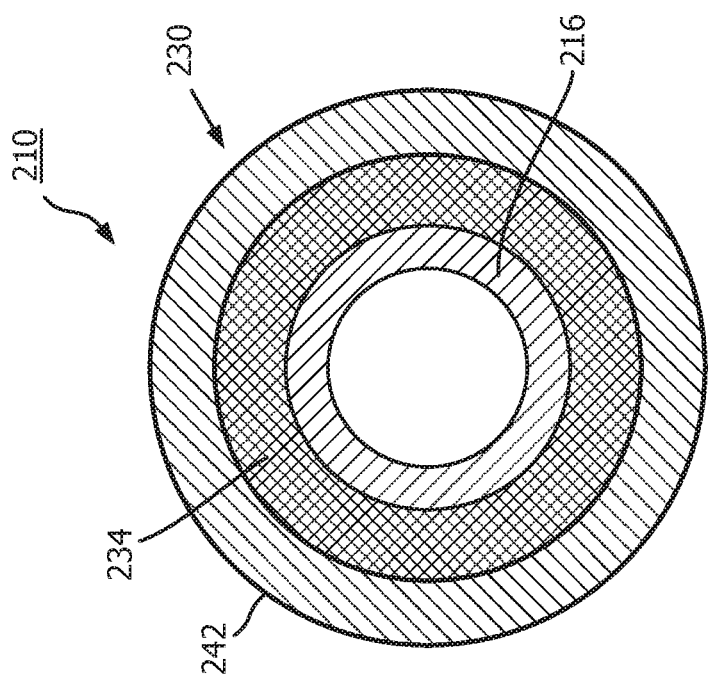
FIG. 4B is a cross sectional view of the therapeutic intermediate member similar to FIG. 3B and including an outer sleeve according to embodiments of the present disclosure.

In this embodiment, the intraluminal ultrasound device 210 includes an ultrasound imaging assembly 220, a therapeutic intermediate member 230 (sometimes referred to herein as "radiating member"), and a flexible elongate member 216 (sometimes referred to herein as "inner member"), which extends from a proximal portion 217 to a distal portion 218 of the intraluminal ultrasound device 210 along the longitudinal axis LA of the ultrasound system 100. The flexible elongate member 216 may be one part of the flexible elongate member 116 (FIG. 1) in some embodiments. For example, the flexible elongate member 216 can be an inner member. An embodiment illustrating inner member 216 and outer member 242 are shown in FIGS. 4A and 4B. As discussed further herein, the intraluminal ultrasound device 210 and the computer 160 (FIG. 1) are in communication with an external ultrasound transducer 250. The external ultrasound transducer 250 can be described as part of ultrasound system 100 and/or the ultrasound structure 130. The external ultrasound transducer 250 can a piezoelectric micromachined ultrasound transducer (PMUT), capacitive micromachined ultrasonic transducer (CMUT), single crystal, lead zirconate titanate (PZT), PZT composite, other suitable transducer type, and/or combinations thereof. In some instances, the intraluminal ultrasound device 210 may also include a treatment component 144 as described with respect to FIG. 1.

In an embodiment, the ultrasound imaging assembly 220 of the intraluminal ultrasound device 210 is disposed at its distal portion 218. In an embodiment, the intraluminal ultrasound device 210 contains a high frequency internal ultrasound transducer 222 positioned within a housing 224. The high frequency internal ultrasound transducer 222 of the ultrasound imaging assembly 220 functions to emit and receive ultrasonic energy at a frequency range between 10 MHz and 70 MHz in situ for the imaging and diagnosis of the lumen 104 of the anatomy 102. The received ultrasonic energy is then transmitted using electrical conductors extending along the length of the flexible elongate member 216 to the ultrasound processing system 160 for processing. The high frequency internal ultrasound transducer 222 of the ultrasound imaging assembly 220 may contain the same features and functionality as described with respect to ultrasound structure 120 as described in FIG. 1.

An attachment mechanism 236, which in some embodiments may be a collar, may be disposed at the distal portion 218 of the intraluminal ultrasound device 210 to facilitate a mechanical connection between the housing 224 of the ultrasound imaging assembly 220 and the therapeutic intermediate member 230. Although FIG. 2A depicts the attachment mechanism 236 as being integrated into the therapeutic intermediate member 230, it is anticipated the attachment mechanism 236 could be a stand-alone apparatus or alternatively be integrated into the housing 224 of the ultrasound imaging assembly 220.

The therapeutic intermediate member 230 is coaxially disposed about or around the flexible elongate member 216 along the longitudinal axis LA adjacent to the imaging assembly 220. For example, the therapeutic intermediate member 230 can be radially or circumferentially positioned around the inner member 216, and/or between the inner member 216 and the outer member 242. As described further herein, the therapeutic intermediate member 230 operates to deliver ultrasound therapeutic energy from the external ultrasound transducer 250 to the lumen 104 of the anatomy 102 at a frequency range between 1 KHz and 5 MHz for the purposes of treating an occlusion 106 observed therein. Accordingly, the therapeutic intermediate member 230 can be made out of any suitable and biocompatible ultrasound medium material that has a minimal wall thickness yet is sturdy and operable to deliver the ultrasound energy efficiently and safely at lower and higher end of the 1 KHz and 5 MHz frequency range. Examples of such materials include but are not limited to stainless steel, nitinol, and aluminum. The therapeutic intermediate member 230 is configured to radiate at one or more frequencies to emit ultrasound energy within the anatomy of the patient. In that regard, the therapeutic intermediate member 230 can be referenced as a radiating member in some instances. An acoustic coupling component 252 may be used to transmit ultrasound Energy from the external ultrasound transducer 250 to the therapeutic intermediate member 230. In some instances, the acoustic coupling component 252 mechanically and/or acoustically couples the external ultrasound transducer 250 to the therapeutic intermediate member 230. FIG. 2A illustrates the acoustic coupling component 252 as a wire. However, the acoustic coupling member may be any mechanical structure used for the efficient transmittance of ultrasound energy as known in the art.

As shown in FIG. 2A, the geometry of an embodiment of the therapeutic intermediate member 230 may include a plurality of peripheral bands 232 spaced along the longitudinal axis LA. The peripheral bands 232 can be extend circumferentially and/or annularly around the longitudinal axis. The peripheral bands 232 comprise surface area that radiates to emit ultrasound energy from the external ultrasound transducer 250 into the anatomy. Various embodiments of the therapeutic intermediate member 230 can include one or a plurality of peripheral bands 232. One or a plurality of a plurality of elongated connecting members 234 may be interposed between the peripheral bands 232. The elongated connecting members 234 may be spaced apart at various radial or peripheral locations around the flexible elongate member 216. The elongated connecting members 234 are configured to be flexible to allow the peripheral bands 232 to radiate/vibrate as needed to emit ultrasound energy of the external ultrasound transducer 250.

In another embodiment, the geometry of the therapeutic intermediate member 230 may include a thin walled super elastic alloy hypo tube, or various pitches of braided/coiled structures.

Figure 2B:
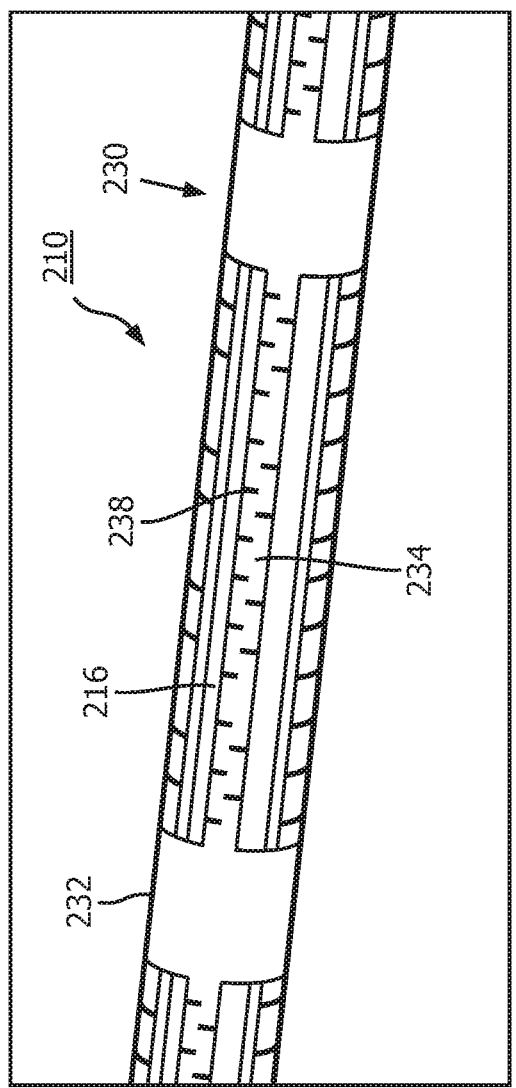
FIG. 2B is an enlarged diagrammatic schematic view of a therapeutic intermediate member of the intraluminal ultrasound device according to embodiments of the present disclosure.

FIG. 2B is an enlarged diagrammatic schematic view of the therapeutic intermediate member 230 as depicted in FIG. 2A. FIG. 2B illustrates each elongated connecting member 234 containing plurality of notches 238. In some embodiments, notches 238 are on opposite sides of the elongated connecting members 234. The therapeutic intermediate member 230 will vibrate, oscillate, and/or otherwise move as result of radiating the ultrasound energy of the external ultrasound transducer 250. The plurality of notches facilitate flexibility in the elongated connecting member 234, thereby allowing the peripheral bands 232 to vibrate, oscillate, and/otherwise move to radiate ultrasound energy. Although FIG. 2B illustrates the notches 238 being positioned on opposite sides along the elongated connecting member 234 in an alternating pattern, the notches can be configured in any pattern that will increase the flexibility of the elongated connecting member 234. Further, although the notches 238 in FIG. 2B are shown as rectangular, it is contemplated that notches 238 may take the form of any polygonal or curvilinear shape. In another embodiment, the therapeutic intermediate member 230 may include elongated connecting members 234 with or without the notches 238.

Figure 3B:
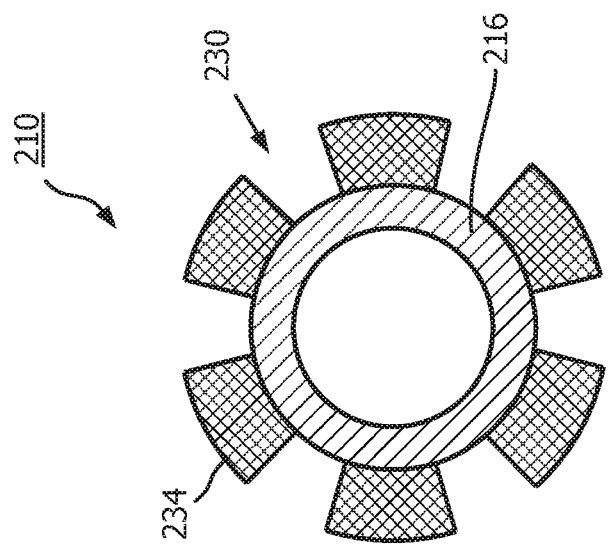
FIG. 3B is a cross sectional view of the therapeutic intermediate member taken along section line 3B-3B according to embodiments of the present disclosure.
Figure 3A:
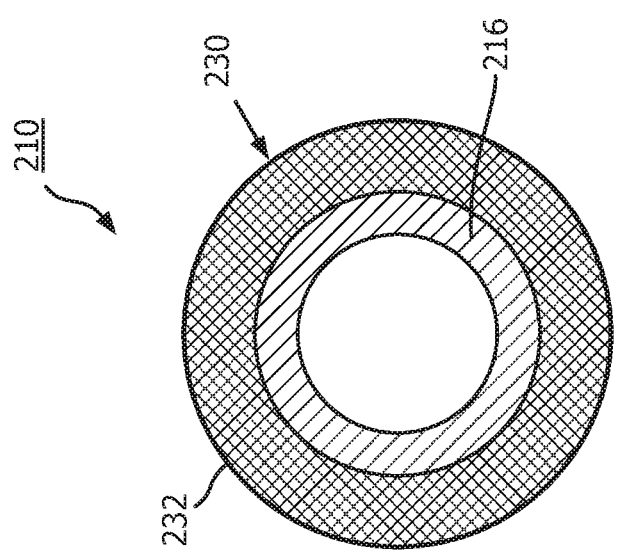
FIG. 3A is a cross sectional view of the therapeutic intermediate member taken section line 3A-3A of FIG. 2A according to embodiments of the present disclosure.

FIGS. 3A and 3B present a cross sectional view of the therapeutic intermediate member 230 taken along section line 3A-3A in FIG. 2A (e.g., along a peripheral band 232) and along section line 3B-3B in FIG. 2A (e.g., an elongated connecting member 234), respectively. As previously discussed, the elements of the therapeutic intermediate member 230 are preferably constructed with minimum wall thickness and therefore it will be appreciated the wall thickness of the peripheral band 232 and the elongated connecting member 234 is for illustrative purposes in FIGS. 3A and 3B. Furthermore, it will be appreciated that the wall thickness of the peripheral band 232 and the elongated connecting member 234 can be larger or smaller than the wall thickness of the flexible elongate member 216 in some embodiments. FIG. 3A depicts the therapeutic intermediate member 230 with a circular cross sectional geometry. However, it will be appreciated that the therapeutic intermediate member 230 may be configured to contain any polygonal or curvilinear cross section and may transition from one to another along the longitudinal axis LA. In some embodiments, the therapeutic intermediate member 230 is in contact with the inner member 216. In other embodiments, the therapeutic intermediate member 230 is radially spaced from the inner member 216.

Although FIG. 3B illustrates the therapeutic intermediate member 230 having six elongated connecting members 234, it will be appreciated in other embodiments that more or fewer elongated connecting members 234 may be used. For example, in some embodiments, the therapeutic intermediate member 230 can have four elongated connecting members 234. Further, the elongated connecting members 234 may be disposed at any radial or peripheral position about the therapeutic intermediate member 230. For example, the elongated connecting members 234 can be symmetrically and/or otherwise equally distributed around a circumference of the therapeutic intermediate member 230. In general, the number, shape, spacing, and/or other structural arrangement of the peripheral bands 232 and/or the elongated connecting members 234 can be based on the frequency of ultrasound energy emitted by the external ultrasound transducer 250. For example, the structural arrangement of the peripheral bands 232 and/or the elongated connecting members 234 can be selected such that the radiating member 230 vibrates in a constructive manner relatively to the ultrasound energy. For example, the structural arrangement of the peripheral bands 232 and/or the elongated connecting members 234 can be based on the harmonics of the frequency of the external ultrasound transducer 250.

Similar to FIGS. 3A and 3B, FIGS. 4A and 4B also present a cross sectional view of the therapeutic intermediate member 230 taken along a peripheral band 232 and an elongated connecting member 234, respectively. However, FIGS. 4A and 4B present the therapeutic intermediate member 230 including an outer sleeve 242 (sometimes referred to herein as "outer member") positioned over the peripheral band 232 and the elongated connecting member 234 respectively. For example, the inner member Although, the outer sleeve 242 is shown as having a circular cross section, it will be appreciated that the outer sleeve 242 may be configured to contain any polygonal or curvilinear cross section and may transition from one to another along the longitudinal axis LA. The outer sleeve 242 is constructed from an acoustically conductive/matching material and functions to enhance emitting the ultrasound energy into the anatomy 102. In some embodiments, the space between the inner member 216 and the outer member 242 can be filled with an acoustically conductive/matching material.

One advantage of the intraluminal ultrasound device 210 having an high frequency internal ultrasound transducer 222 and an external ultrasound transducer 250 is the alleviation of spatial constraints and rigidity caused by the placement of two transducers within the anatomy 102 on the intraluminal ultrasound device 210. Removing one transducer of the intraluminal ultrasound device 210 significantly reduces the complexity of its design and manufacturing. Further, the use of an external ultrasound therapeutic transducer 250 in conjunction with a therapeutic intermediate member 230 opens the possibility for the intraluminal ultrasound device 210 to operate with low frequency ranges typically reserved for larger transducer. Because the external transducer is positioned outside of the body, a larger transducer can be used without the space constraints of being positioned within the body of the patient.

Figure 5:
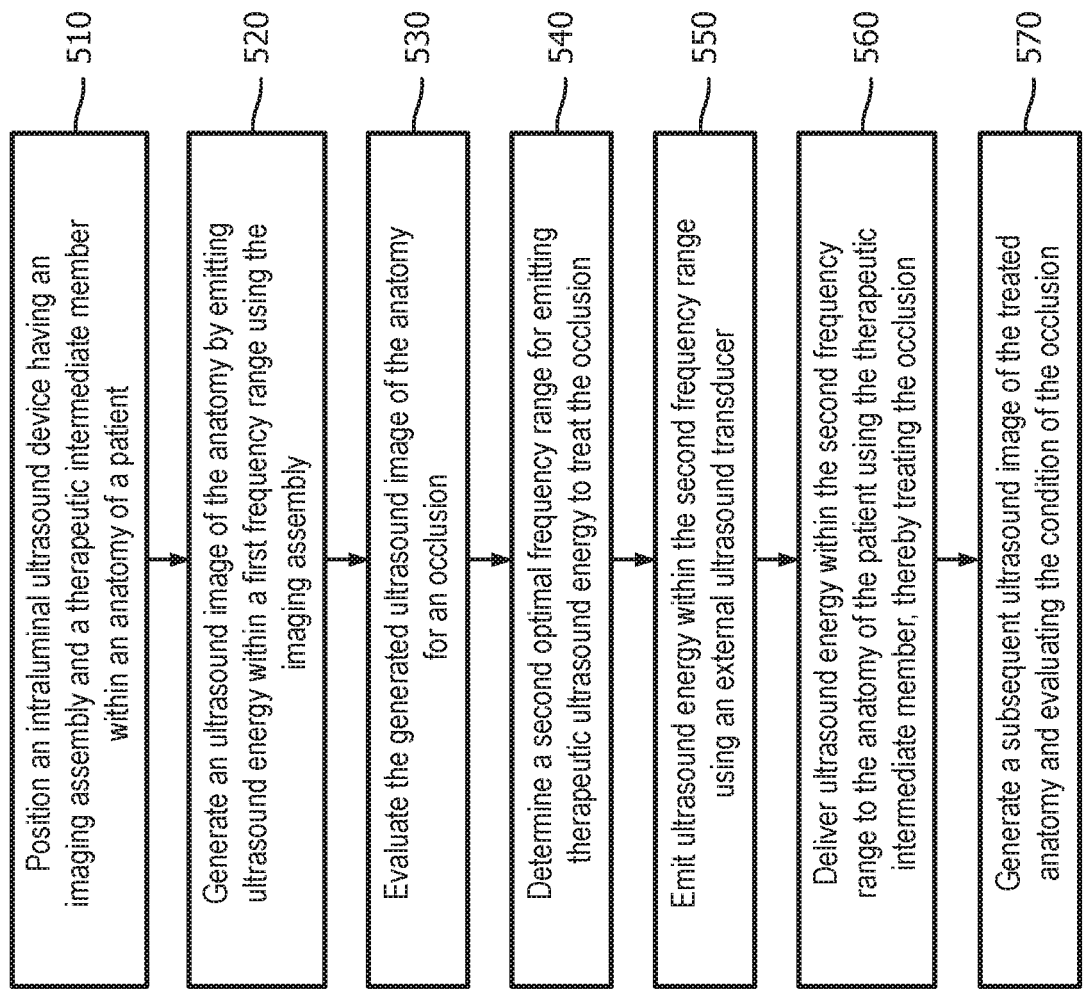
FIG. 5 is a flow diagram of a method of preparing an anatomy of a patient for a pharmacological treatment according to embodiments of the present disclosure.

FIG. 5 is a flow diagram of a method 500 for preparing an anatomy of a patient for a pharmacological treatment according to an embodiment of the present disclosure. Method 500 begins in step 510 by positioning an intraluminal ultrasound device 210 having an ultrasound imaging assembly 220 and a therapeutic intermediate member 230 within an anatomy 102 of a patient. A guide wire 140 extending through a lumen or the flexible elongate member 216 of the intraluminal ultrasound device 210, may be used to position the ultrasound imaging assembly 220 and the therapeutic intermediate member 230 at desired location within a lumen 104 of anatomy 102 of the patient.

In step 520, an ultrasound image of the anatomy 102 is generated by emitting ultrasound energy within a first frequency range using the ultrasound imaging assembly 220. The ultrasound imaging assembly 220 contains an high frequency internal ultrasound transducer 222 which can be configured to generate and emit ultrasound energy into the anatomy 102 in response to being activated by an electrical signal. The high frequency internal ultrasound transducer 222 may be any suitable configuration such as rotational or phased array including a planar array, a curve array, a circumferential array, an annular array, etc. For imaging, the high frequency internal ultrasound transducer 222 generates and transmits an electrical signal representative of the received reflected ultrasound echoes from the anatomy 102 (e.g., to the PIM 150 and/or computer 160). The center frequency of the first frequency range emitted by high frequency internal ultrasound transducer 222 may be between between 10 MHz and 70 MHz. In some embodiments, the frequency of high frequency internal ultrasound transducer 222 is tuneable. For imaging, in some instances, the high frequency internal ultrasound transducer 222 may be tuned to receive wavelengths associated with the center frequency and/or one or more harmonics of the center frequency. In some instances, the frequency of the emitted ultrasonic energy may be modified by the voltage of the applied electrical signal and/or the application of a biasing voltage to the high frequency internal ultrasound transducer 222.

In step 530, the ultrasound image of the anatomy 102 generated by the ultrasound imaging assembly 220 is evaluated using virtual histology (VH) or other algorithms to determine whether an occlusion 106 is present and/or the composition of the occlusion. These methods may be used to quantify the magnitude (i.e., diameter) and the hardness (i.e., calcification) occlusion 106.

Detecting and characterizing plaque using IVUS with VH are described in, for example, U.S. Pat. No. 6,200,268 entitled "VASCULAR PLAQUE CHARACTERIZATION" issued Mar. 13, 2001 with D. Geoffrey Vince, Barry D. Kuban and Anuja Nair as inventors, 6,381,350 entitled "INTRAVASCULAR ULTRASONIC ANALYSIS USING ACTIVE CONTOUR METHOD AND SYSTEM" issued Apr. 30, 2002 with Jon D. Klingensmith, D. Geoffrey Vince and Raj Shekhar as inventors, 7,074,188 entitled "SYSTEM AND METHOD OF CHARACTERIZING VASCULAR TISSUE" issued Jul. 11, 2006 with Anuja Nair, D. Geoffrey Vince, Jon D. Klingensmith and Barry D. Kuban as inventors, 7,175,597 entitled "NON-INVASIVE TISSUE CHARACTERIZATION SYSTEM AND METHOD" issued Feb. 13, 2007 with D. Geoffrey Vince, Anuja Nair and Jon D. Klingensmith as inventors, 7,215,802 entitled "SYSTEM AND METHOD FOR VASCULAR BORDER DETECTION" issued May 8, 2007 with Jon D. Klingensmith, Anuja Nair, Barry D. Kuban and D. Geoffrey Vince as inventors, 7,359,554 entitled "SYSTEM AND METHOD FOR IDENTIFYING A VASCULAR BORDER" issued Apr. 15, 2008 with Jon D. Klingensmith, D. Geoffrey Vince, Anuja Nair and Barry D. Kuban as inventors and 7,463,759 entitled "SYSTEM AND METHOD FOR VASCULAR BORDER DETECTION" issued Dec. 9, 2008 with Jon D. Klingensmith, Anuja Nair, Barry D. Kuban and D. Geoffrey Vince, as inventors, the teachings of which are hereby incorporated by reference herein in their entireties.

In step 540, based upon the evaluation of the ultrasound image produced by the ultrasound imaging assembly 220, a parameter for the ultrasound therapy is determined, such as a second optimal frequency range for emitting therapeutic ultrasound energy. In an embodiment, the center frequency for the second optimal frequency range is lower than the first frequency range used for imaging and may be between 1 kHz and 5 MHz. In some instances, the second optimal frequency range may be arrived at by determining a pulse amplitude and a pulse length for the ultrasound energy in either an automated or user controlled process. In that regard, the method 500 can include controlling, by the computer (e.g., computer 160 of FIG. 1), the external ultrasound transducer to emit ultrasound energy based on the determined parameter.

In step 550, ultrasound energy within the second frequency range is emitted using an external ultrasound transducer 250. Similar to the operation of the high frequency internal ultrasound transducer 222 of the ultrasound imaging assembly 220, the external ultrasound transducer 250 may be configured to generate and emit ultrasound energy in response to being activated by an electrical signal. The external ultrasound transducer 250 functions to emit ultrasound energy within the frequency range between 1 kHz and 5 MHz.

In step 560, ultrasound energy within the second frequency range is delivered to anatomy 102 of the patient using the therapeutic intermediate member 230 to treat the occlusion 106. An acoustic coupling component 252 may be used to transmit it ultrasound energy emitted from the external ultrasound transducer 250 to the therapeutic intermediate member 230. The therapeutic intermediate member 230 may be configured to emit the ultrasound energy from multiple locations along the longitudinal axis LA into the anatomy 102. For instance, the therapeutic intermediate member 230 may configured to emit ultrasonic energy from each of the peripheral bands 232 and elongated connecting members 234. Alternatively, the therapeutic intermediate member 230 may be configured to only emit ultrasonic energy from the peripheral bands 232. In an alternative embodiment, the attachment mechanism 236 may be used to direct ultrasonic energy to a desired location within the anatomy 102. Emitting ultrasound energy to the anatomy 102 containing the occlusion 106 may result in damaging the structure of the occlusion 106. For instance, the ultrasonic energy emitted by therapeutic intermediate member 230 may create micro fractures or cavitation (e.g., wave force cavitation, thermal cavitation, etc.) in the occlusion 106. These micro fractures or cavitations may be advantageous in creating additional surface area for a pharmacological agent to contact and/or penetrate the anatomy 102.

Finally, in step 570, a subsequent ultrasound image of the treated anatomy 102 of the patient is generated. The subsequent ultrasound image may be generated in manner similar to as described in step 520. The subsequent ultrasound imaged may then be evaluated to determine the effectiveness of the therapeutic treatment in damaging the occlusion 106 in a manner similar to as described in step 530. Depending of the outcome of the evaluation, further treatment of the anatomy 102 or occlusion 106 may be performed using a treatment component 144 in a manner similar to as described with respect to FIG. 1. For example, a pharmacological agent can be applied to the anatomy.

The systems, devices, and methods of the present disclosure can include features described in U.S. Provisional App. No. 62/545,951, filed on an even date herewith, U.S. Provisional App. No. 62/545,954, filed on an even date herewith, U.S. Provisional App. No. 62/545,927, filed on an even date herewith, and/or U.S. Provisional App. No. 62/545,888, filed on an even date herewith, the entireties of which are hereby incorporated by reference herein.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound device, comprising:
a flexible elongate member configured to be inserted into a lumen of a patient, the flexible elongate member comprising a proximal portion and a distal portion;
an ultrasound imaging assembly disposed at the distal portion of the flexible elongate member and configured to obtain imaging data while positioned within the lumen of the patient, the ultrasound imaging assembly having a proximal-most end;
a transducer; and
an intermediate member coaxially disposed around an exterior of the flexible elongate member and extending lengthwise along a length the flexible elongate member proximal from the proximal-most end of the ultrasound imaging assembly, the intermediate member being mechanically and acoustically coupled to the transducer,
wherein the intermediate member has a plurality of vibrational bands that are spaced apart along a length of the flexible elongate member proximally of the ultrasound imaging assembly, and a plurality of flexible connecting regions extending along the length of the flexible elongate member between respective adjacent pairs of the vibrational bands, the flexible connecting regions are more flexible than the vibrational bands, and the vibrational bands are configured to emit acoustic energy in response to the transducer for therapeutic treatment within the lumen of the patient.

2. The intraluminal ultrasound device of claim 1, wherein the ultrasound imaging assembly comprises at least one of circumferential transducer array, a planar transducer array, or a rotating transducer.

3. The intraluminal ultrasound device of claim 1, wherein the ultrasound imaging assembly is configured to emit ultrasound energy at a frequency range between 10 MHz and 70 MHz.

4. The intraluminal ultrasound device of claim 1, wherein the transducer is configured to vibrate the vibrational bands of the intermediate member at a frequency range between at least 20 KHz and 5 MHz.

5. The intraluminal ultrasound device of claim 1, wherein each of the flexible connecting regions is defined by surface deformations formed in an outer surface of the intermediate member between adjacent vibrational bands, and wherein the vibrational bands are devoid of surface deformations.

6. The intraluminal ultrasound device of claim 5, wherein the surface deformations include notches formed in the outer surface of the intermediate member.

7. An intraluminal ultrasound device, comprising:
a flexible elongate member configured to be inserted into a lumen of a patient, the flexible elongate member comprising a proximal portion and a distal portion;
an ultrasound imaging transceiver disposed at the distal portion of the flexible elongate member, the ultrasound transceiver having a proximal-most end;
an intermediate member coaxially disposed around an exterior of the flexible elongate member and extending lengthwise along a length of the flexible elongate member proximal from the proximal-most end of the ultrasound imaging transceiver,
wherein the intermediate member has a plurality of vibrational bands that are spaced apart along a length of the flexible elongate member, and a plurality of flexible connecting regions extending along the length of the flexible elongate member between respective adjacent pairs of the vibrational bands, the flexible connecting regions are more flexible than the vibrational bands, and the vibrational bands are configured to emit acoustic energy for therapeutic treatment within the lumen of the patient.

8. The intraluminal ultrasound device of claim 1, wherein the intermediate member is made of stainless steel, nitinol, or aluminum.

9. The intraluminal ultrasound device of claim 7, wherein the intermediate member is made of stainless steel, nitinol, or aluminum.

10. The intraluminal ultrasound device of claim 1, wherein the intermediate member comprises an elastic alloy hypo tube.

11. The intraluminal ultrasound device of claim 7, wherein the intermediate member comprises an elastic alloy hypo tube.

12. The intraluminal ultrasound device of claim 1, wherein outer surface portions of the flexible elongate member are exposed through the intermediate member in each of the flexible connecting regions.

13. The intraluminal ultrasound device of claim 5, wherein outer surface portions of the flexible elongate member are exposed through at least some of the deformations formed in the outer surface of the intermediate member.

14. The intraluminal ultrasound device of claim 1, wherein a length of each of vibrational bands in the longitudinal direction is less than a length of each of the flexible connection regions in the longitudinal direction.

15. The intraluminal ultrasound device of claim 1, further comprising an acoustically conductive outer sleeve coaxially disposed around an exterior of the intermediate member and extending lengthwise along a length of the intermediate member.

16. The intraluminal ultrasound device of claim 7, wherein each of the flexible connecting regions is defined by surface deformations formed in an outer surface of the intermediate member between adjacent vibrational bands, and wherein the vibrational bands are devoid of surface deformations.

17. The intraluminal ultrasound device of claim 16, wherein the surface deformations include notches formed in the outer surface of the intermediate member.

18. The intraluminal ultrasound device of claim 7, wherein outer surface portions of the flexible elongate member are exposed through the intermediate member in each of the flexible connecting regions.

19. The intraluminal ultrasound device of claim 16, wherein outer surface portions of the flexible elongate member are exposed through at least some of the deformations formed in the outer surface of the intermediate member.

20. The intraluminal ultrasound device of claim 7, wherein a length of each of vibrational bands in the longitudinal direction is less than a length of each of flexible connecting regions in the longitudinal direction.

21. The intraluminal ultrasound device of claim 7, further comprising an acoustically conductive outer sleeve coaxially disposed around an exterior of the intermediate member and extending lengthwise along a length of the intermediate member.

* * * * *